United States Patent
Shchekin et al.

(10) Patent No.: US 11,969,238 B2
(45) Date of Patent: Apr. 30, 2024

(54) PHYSIOLOGICAL PARAMETER DETECTING APPARATUS AND METHOD OF DETECTING PHYSIOLOGICAL PARAMETERS

(71) Applicant: SAMSUNG ELECTRONICS CO., LTD., Suwon-si (KR)

(72) Inventors: Alexey Andreevich Shchekin, Moscow (RU); Maxim Vladimirovich Riabko, Moscow (RU); Anton Sergeevich Medvedev, Moscow (RU); Alexey Dmitrievich Dmitrievich Lantsov, Moscow (RU); Sergey Nikolaevich Koptyaev, Sverdlovskaya (RU)

(73) Assignee: SAMSUNG ELECTRONICS CO., LTD., Suwon-si (KR)

( * ) Notice: Subject to any disclaimer, the term of this patent is extended or adjusted under 35 U.S.C. 154(b) by 514 days.

(21) Appl. No.: 17/235,404

(22) Filed: Apr. 20, 2021

(65) Prior Publication Data

US 2021/0236007 A1    Aug. 5, 2021

Related U.S. Application Data

(63) Continuation of application No. 15/581,695, filed on Apr. 28, 2017, now Pat. No. 11,045,103.

(30) Foreign Application Priority Data

Apr. 28, 2016 (RU) .......................... RU2016116865
May 9, 2016 (KR) ........................ 10-2016-0056610

(51) Int. Cl.
*A61B 5/026* (2006.01)
*A61B 5/00* (2006.01)
(Continued)

(52) U.S. Cl.
CPC ........ *A61B 5/0261* (2013.01); *A61B 5/02427* (2013.01); *A61B 5/14552* (2013.01);
(Continued)

(58) Field of Classification Search
CPC . A61B 5/0261; A61B 5/14552; A61B 5/7278; A61B 5/742; A61B 2560/0214;
(Continued)

(56) References Cited

U.S. PATENT DOCUMENTS

| 3,706,939 A | 12/1972 | McLafferty |
| 5,241,551 A | 8/1993 | Chernoch et al. |

(Continued)

FOREIGN PATENT DOCUMENTS

| KR | 1020160025286 A | 3/2016 |
| RU | 2 354 290 C1 | 5/2009 |
| RU | 2 567 834 C1 | 11/2015 |

OTHER PUBLICATIONS

Office Action issued in Russian Application No. 2016116865/14(026493) dated Mar. 1, 2017.
(Continued)

*Primary Examiner* — Baisakhi Roy
(74) *Attorney, Agent, or Firm* — Sughrue Mion, PLLC

(57) ABSTRACT

Physiological parameter detecting apparatuses and methods of detecting the physiological parameters are provided. A physiological parameter detecting apparatus includes: a light source configured to emit a light onto a region of an object; an optical path converter configured to receive the light returning from the object and convert an optical path of the received light; an optical detector configured to detect the light that has the converted optical path; and a controller configured to extract physiological information of the object from the detected light.

9 Claims, 4 Drawing Sheets

(51) Int. Cl.
*A61B 5/024* (2006.01)
*A61B 5/1455* (2006.01)

(52) U.S. Cl.
CPC ............ *A61B 5/7278* (2013.01); *A61B 5/742* (2013.01); *A61B 2560/0214* (2013.01); *A61B 2560/0475* (2013.01); *A61B 2562/0233* (2013.01); *A61B 2562/0238* (2013.01); *A61B 2562/043* (2013.01); *A61B 2562/046* (2013.01); *A61B 2576/00* (2013.01)

(58) Field of Classification Search
CPC .... A61B 2560/0475; A61B 2562/0238; A61B 2562/046; A61B 2576/00
See application file for complete search history.

(56) References Cited

U.S. PATENT DOCUMENTS

| | | | |
|---|---|---|---|
| 6,413,223 | B1 | 7/2002 | Yang et al. |
| 6,599,251 | B2 | 7/2003 | Chen et al. |
| 6,654,163 | B1* | 11/2003 | Du .................... H01S 3/2325 |
| | | | 359/347 |
| 6,932,772 | B2 | 8/2005 | Kan |
| 8,467,636 | B2 | 6/2013 | Borgos et al. |
| 11,045,103 | B2* | 6/2021 | Shchekin ............. A61B 5/0261 |
| 2003/0227681 | A1 | 12/2003 | Currie |
| 2004/0165640 | A1 | 8/2004 | Clifford, Jr. et al. |
| 2005/0249258 | A1 | 11/2005 | Rothenberg et al. |
| 2006/0111634 | A1 | 5/2006 | Wu |
| 2007/0287927 | A1 | 12/2007 | Borgos |
| 2008/0080584 | A1 | 4/2008 | Coyle |
| 2010/0197038 | A1 | 8/2010 | Verschuren |
| 2011/0288421 | A1 | 11/2011 | Banet et al. |
| 2012/0296184 | A1 | 11/2012 | LeBoeuf et al. |
| 2013/0281865 | A1* | 10/2013 | Kang .................... A61B 5/742 |
| | | | 600/476 |
| 2014/0148658 | A1 | 5/2014 | Zalevsky et al. |
| 2014/0163387 | A1* | 6/2014 | Kang ................... A61B 5/0071 |
| | | | 600/476 |
| 2014/0204382 | A1 | 7/2014 | Christensen |
| 2014/0378794 | A1 | 12/2014 | Conrad et al. |
| 2015/0119657 | A1* | 4/2015 | LeBoeuf .............. A61B 5/0013 |
| | | | 600/478 |
| 2016/0058381 | A1 | 3/2016 | Lee et al. |
| 2016/0097716 | A1 | 4/2016 | Gulati et al. |
| 2016/0198961 | A1* | 7/2016 | Homyk .................. A61B 5/681 |
| | | | 600/476 |
| 2016/0327414 | A1* | 11/2016 | Sanzari .............. G01D 5/35312 |
| 2016/0369332 | A1* | 12/2016 | Rothberg .............. H01S 3/1305 |
| 2019/0076036 | A1* | 3/2019 | Lasarov ................... G02B 6/08 |

OTHER PUBLICATIONS

Soleymani, S. M. Ali. Design and analysis of micro-mirror based tunable optical delay line [online], McGill University (Canada), ProQuest Dissertations Publishing, 2004 [retrieved on Dec. 2, 2019], Order No. MR06588. Retrieved from the Internet: <URL: see Office action>. (Year: 2004).

Communication dated Nov. 25, 2022 issued by the Korean Intellectual Property Office in application No. 10-2016-0056610.

\* cited by examiner

PHYSIOLOGICAL PARAMETER DETECTING APPARATUS AND METHOD OF DETECTING PHYSIOLOGICAL PARAMETERS

CROSS-REFERENCE TO RELATED APPLICATIONS

This is a continuation application of U.S. application Ser. No. 15/581,695, filed Apr. 28, 2017, which claims priority from Russian Patent Application No. 2016116865, filed on Apr. 28, 2016 in the Russian Federal Service for Intellectual Property, and Korean Patent Application No. 10-2016-0056610, filed on May 9, 2016 in the Korean Intellectual Property Office, the disclosures of which are incorporated herein by reference in their entireties.

BACKGROUND

1. Field

Apparatuses and methods consistent with exemplary embodiments relate to detecting physiological parameters.

2. Description of the Related Art

As the interest in health increases, various kinds of apparatuses for measuring and detecting physiological information have been developed. In particular, since various wearable devices configured to be directly worn on an object are developed, equipment specialized in health care have been developed. In order to perform correct physiological information analysis, various kinds of instrumental or algorithmic techniques have been studied.

In order to determine a physical situation of an object, physiological information to be measured by using a physiological information measuring apparatus, that is, human physiological parameters may be, for example, blood pressure, pulse rate, heartbeat, and blood glucose. These physiological parameters do not have constant values but continuously change, and accordingly, may need to be continuously monitored. For example, blood pressure and heart rate may be the cause of cardiovascular disorders, such as high blood pressure, low blood pressure, and heart attack. Thus, correct measurement and the continuous monitoring of the physiological parameters may play a very important role in the prevention and curing of disease that may be suffered by the object. In order to measure and monitor the continuous changes of the physiological parameters of the object, there is a need to develop a method of easily accessing the object in a non-invasive atmosphere.

SUMMARY

One or more exemplary embodiments provide physiological parameter detecting apparatuses configured to non-invasively detect and analyze physiological parameters of an object.

Further, one or more exemplary embodiments provide methods of detecting the physiological parameters by using the physiological parameter detecting apparatuses.

According to an aspect of an exemplary embodiment, a physiological parameter detecting apparatus includes: an optical irradiation unit configured to irradiate a first light onto a region of an object; an optical path conversion unit configured to convert an optical path of a second light by receiving the second light emitted from the object; an optical detector configured to detect light, the optical path of which is converted by the optical path conversion unit; and a controller configured to detect physiological information of the object.

The optical irradiation unit may further be configured to irradiate a coherent wave to the object.

The first light emitted from the optical irradiation unit may have a wavelength in a range from about 400 nm to about 700 nm.

The first light emitted from the optical irradiation unit may have a wavelength in a range from about 700 nm to about 1500 nm.

The optical path conversion unit may further be configured to convert, extend, or delay the optical path of the second light.

The optical path conversion unit may include reflection surfaces configured to reflect the second light.

The optical path conversion unit may include at least two reflection surfaces that reflect the second light and the reflection surfaces may be arranged to form an acute angle to each other.

The reflection surfaces may be arranged to face each other.

The optical detector may include a pixel array detector, and a plurality of image sensors arranged in a one-dimensional (1D) structure or a two-dimensional (2D) structure.

The optical detector may include a position sensitive detector (PSD) having at least two unit sensors spatially separated from each other.

The controller may include a data processor, a memory, a display, and a battery.

According to an aspect of an embodiment, a method of detecting physiological information of an object, the method includes: emitting, from an optical irradiation unit, a first light onto a region of the object; detecting, by an optical detector, a speckle pattern of a second light after converting an optical path of the second light that is generated from the object by emitting and scattering the first light; and detecting the physiological information of the object from the speckle pattern of the second light.

The method may further include emitting the first light having a wavelength in a range from about 400 nm to about 700 nm and detecting, by the optical detector, a speckle pattern of a skin surface of the object.

The method may further include emitting the first light having a wavelength in a range from about 700 nm to about 1500 nm and detecting, by the optical detector, a speckle pattern of a skin surface of the object.

The method may further include converting or extending, by the optical path conversion unit, an optical path of the second light by reflecting the second light using reflection surfaces.

According to an aspect of an exemplary embodiment, there is provided a physiological parameter detecting apparatus including: a light source configured to emit a light onto a region of an object; an optical path converter configured to receive the light returning from the object and convert an optical path of the received light; an optical detector configured to detect the light that has the converted optical path; and a controller configured to extract physiological information of the object from the detected light.

The light source may be further configured to emit a coherent wave to the object.

The light emitted from the light source may have a wavelength in a range from about 400 nm to about 700 nm.

The light emitted from the light source may have a wavelength in a range from about 700 nm to about 1500 nm.

The optical path converter may be further configured to convert, extend, or delay the optical path of the received light.

The optical path converter may include reflection surfaces configured to reflect the received light.

The optical path converter may include at least two reflection surfaces that reflect the received light, and the reflection surfaces may be arranged to form an acute angle to each other.

The reflection surfaces may be arranged to face each other.

The optical detector may include a pixel array detector and a plurality of image sensors arranged in a one-dimensional (1D) structure or a two-dimensional (2D) structure.

The optical detector may include a position sensitive detector (PSD) including at least two unit sensors spatially separated from each other.

The controller may include a data processor, a memory, a display, and a battery.

According to an aspect of another exemplary embodiment, there is provided a method of detecting physiological information of an object. The method may include: emitting a light onto a region of the object; receiving the light returning from the object; converting an optical path of the received light; detecting a speckle pattern of the light that has the converted optical path; and detecting the physiological information of the object from the speckle pattern of the light.

The emitted light may have a wavelength in a range from about 400 nm to about 700 nm, and the detected speckle pattern may indicate a speckle pattern of a skin surface of the object.

The emitted light may have a wavelength in a range from about 700 nm to about 1500 nm, and the detected speckle pattern may indicate a speckle pattern of a skin surface of the object.

The method may further include: reflecting the received light using reflection surfaces to convert or extend the optical path of the received light.

BRIEF DESCRIPTION OF THE DRAWINGS

The above and/or other aspects will be more apparent by describing certain exemplary embodiments, with reference to the accompanying drawings, in which.

DETAILED DESCRIPTION

Figure 1:
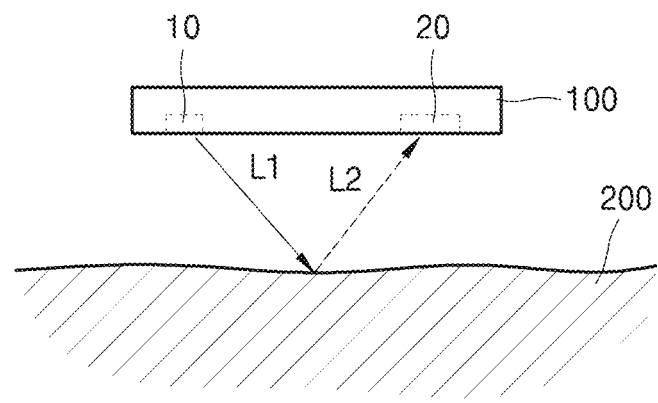
FIG. 1 is a schematic drawing of a physiological information measuring apparatus (hereinafter, referred to as an apparatus), according to an exemplary embodiment.

Exemplary embodiments are described in greater detail below with reference to the accompanying drawings.

In the following description, like drawing reference numerals are used for like elements, even in different drawings. The matters defined in the description, such as detailed construction and elements, are provided to assist in a comprehensive understanding of the exemplary embodiments. However, it is apparent that the exemplary embodiments can be practiced without those specifically defined matters. Also, well-known functions or constructions are not described in detail since they would obscure the description with unnecessary detail.

FIG. 1 is a schematic drawing of a physiological information measuring apparatus 100 according to an exemplary embodiment.

Referring to FIG. 1, the apparatus 100 may include an optical irradiation unit 10 configured to emit light L1 to a region of an object 200 and an optical path conversion unit 20 configured to convert an optical path by receiving light L2 scattered and emitted from the object 200 by the light L1 emitted to the object 200. The optical irradiation unit 10 may be embodied by a light source or a light emitter. Also, the apparatus 100 may include an optical detector 30 that convert an optical signal to an electrical signal by receiving light L2 converted by the optical path conversion unit 20. The optical detector 30 may be also referred to as an optical sensor. The combination of the optical irradiation unit 10 and the optical path conversion unit 20, or the combination of the optical irradiation unit 10, the optical path conversion unit 20, and the optical detector 30 may be implemented by a spectrometer. Also, the apparatus 100 may further include a controller 40 that controls the optical irradiation unit 10 and analysis the state of the object 200 by using physiological parameters that are detected from the light L2 that is scattered, deflected, or reflected from the object 200. The controller 40 may be embodied by a processor.

Here, object 200 has a surface at which light L1 emitted from the optical irradiation unit 10 of the apparatus 100 is scattered, may be a human body or an animal and may include a portion of a human body or an animal.

The apparatus 100 according to the current exemplary embodiment may measure physiological information of the object 200 by being separated from the object 200, but not limited thereto, that is, may measure the physiological parameters in contact with the object 200. Also the apparatus 100 may be used by being mounted in a mobile device or as an independent device as a prototype. The apparatus 100 may be used by being attached to a specific portion, for example, hands, arms, legs, feet, wrists, elbows, shoulders, back, neck, waist, or ears, and may be used as a wearable device type by being inserted into a cloth.

Figure 2:
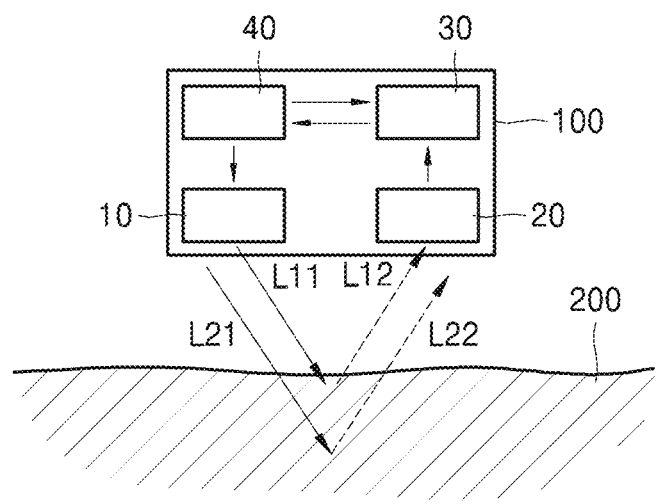
FIG. 2 is a schematic cross-sectional view for explaining a method of detecting light scattered from an object, according to an exemplary embodiment.

FIG. 2 is a schematic cross-sectional view of a method of detecting scattered light L12 and L22 emitted from an object by the apparatus 100 after emitting light L11 and L21 onto the object 200 from the apparatus 100 according to an exemplary embodiment.

Referring to FIG. 2, light L11 and L21 emitted from the optical irradiation unit 10 of the apparatus 100 may enter the optical path conversion unit 20 by scattering at a surface or inside of the object 200. Here, the light L11 and L21 irradiated emitted from the optical irradiation unit 10 is referred to as a first optical irradiation, and the light L12 and L22 scattered by the object 200 is referred to as a second optical irradiation. The optical irradiation unit 10 may emit a coherent wave onto the object 200, for example, the optical irradiation unit 10 may be a laser. A beam shaper may be located on a region where the first optical irradiation L11 and L21 is emitted from the optical irradiation unit 10.

The first optical irradiation L11 and L21 emitted from the optical irradiation unit 10 may be light having various ranges of wavelengths, and the wavelength range of the first optical irradiation L11 and L21 may be selected by the user. For example, in order to obtain physiological information of a surface of a skin of the object 200, the wavelength of the first optical irradiation L11 emitted from the optical irradiation unit 10 may be selected in a range from about 400 nm to about 600 nm so that the first optical irradiation L11 emitted from the optical irradiation unit 10 is reflected by the skin surface of the object 200, and thus, the second optical irradiation L12 is obtained. When the first optical irradiation L11 having the wavelength range is emitted from the optical irradiation unit 10 onto the object 200, the first optical irradiation L11 is scattered at the skin surface of the object 200 without invading into the skin of the object 200, and thus, the second optical irradiation L12 is emitted. If the first optical irradiation L11 has a wavelength range of 400 nm to 600 nm or 400 nm to 700 nm and when the first optical irradiation L11 is emitted onto the object 200 from the optical irradiation unit 10, an invasion depth from the skin surface of the object 200 is limited to approximately in a range from about 200 um to about 300 um. Accordingly, the second optical irradiation L12 having state information at a skin of the object 200 may be emitted without affecting a blood vessel of the skin or blood flow in the blood vessel.

Also, if a near infrared ray or wavelength in a range from about 700 nm to about 1,500 nm which is an infrared range is selected as the wavelength range of the first optical irradiation L21 emitted from the optical irradiation unit 10, the first optical irradiation L21 is reflected and scattered at a region where a blood vessel is present in the skin of the object 200, and thus, the second optical irradiation L22 may be obtained. When the first optical irradiation L21 having a wavelength of infrared ray or near infrared ray is emitted to the object 200 from the optical irradiation unit 10, the first light L21 is scattered by red blood cells (RBCs) in the blood vessel, and thus, the second light is generated. Accordingly, if near infrared ray or a wavelength range from about 700 nm to about 1,500 nm which is infrared ray region is used as the first light L21, the second light L12 generated at the skin surface may be minimized. Also, this range of first light L21 is effective to obtain physiological information related to RBCs, blood flow velocity, and blood oxygenation in the blood vessel.

Figure 3:
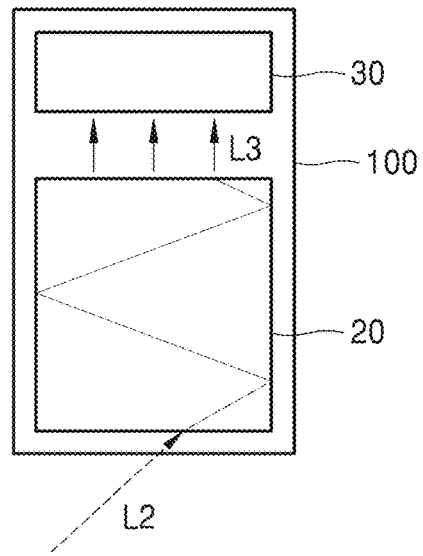
FIG. 3 is a schematic drawing for explaining a method of detecting light scattered from an object by using an optical path conversion unit and a detector of the apparatus, according to an exemplary embodiment.

FIG. 3 is a schematic drawing of a method of detecting light scattered from the object 200 by using the optical path conversion unit 20 and a detector of the apparatus 100 according to an exemplary embodiment.

Referring to FIGS. 1 and 3, a second light L2 scattered from a region of the object 200 enters the optical path conversion unit 20. An optical path of the second light L2 entered the optical path conversion unit 20 may be converted in the optical path conversion unit 20. The optical path conversion unit 20 may extend an optical path of the second light L2 by changing the optical path of the second light L2. In the optical path conversion unit 20, the second light L2 may be changed to a state suitable to detect physiological parameters of the object 200. The second light L2 scattered from the object 200 may include speckle pattern information of a region of the object 200 where the first light is scattered. It is necessary to secure an optical path of the second light L2 to be an optimum condition for correctly measuring the physiological parameters of the object 200, and accordingly, the optical path conversion and extension of the second light L2 may be performed by the optical path conversion unit 20. The optical path conversion unit 20 may be an optical delay line for optical path conversion and extension of the second light L2. The second light L2 may enter the optical detector 30 as light L3 which is the second light L2, the optical path of which is changed by the optical path conversion unit 20. The optical path conversion unit 20 of the apparatus 100 according to the current exemplary embodiment may include reflection surfaces to convert and extend the optical path of the second light L2, which will be described with reference to FIGS. 4A and 4B.

Figure 4A:
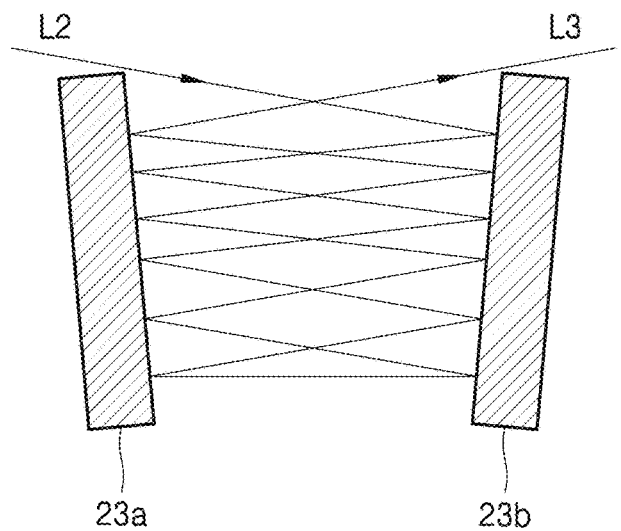
FIGS. 4A and 4B are cross-sectional views of an optical path conversion unit of the apparatus, according to an exemplary embodiment.
Figure 4B:
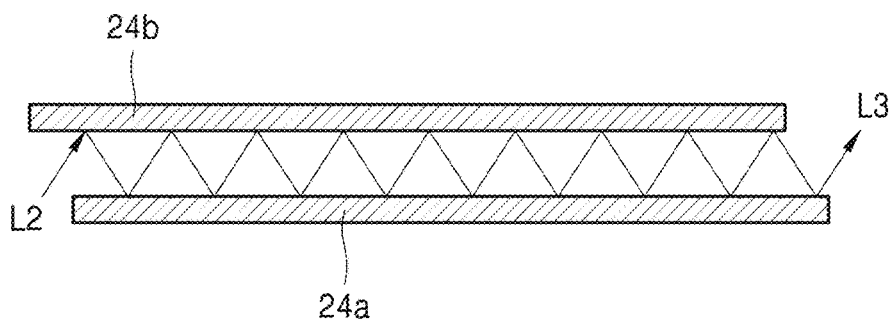

FIGS. 4A and 4B are cross-sectional views of the optical path conversion unit 20 of the apparatus according to an exemplary embodiment.

Referring to FIGS. 3 and 4A, the optical path conversion unit 20 may include a first reflection surface 23a and a second reflection surface 23b that are configured to reflect the second light L2, and an angle between the first reflection surface 23a and the second reflection surface 23b form a very small acute angle. In this case, the second light L2 entering the optical path conversion unit 20 proceeds towards the optical detector 30 after reciprocally reflecting between the first reflection surface 23a and the second reflection surface 23b a plurality of times.

Also, referring to FIGS. 3 and 4B, the optical path conversion unit 20 may include a third reflection surface 24a and a fourth reflection surface 24b that are configured to reflect the second light L2. The third reflection surface 24a and the fourth reflection surface 24b are arranged substantially parallel to each other, and the third reflection surface 24a and the fourth reflection surface 24b may face each other. If the optical path conversion unit 20 has an arrangement structure as described above, the second light L2 enters between the third reflection surface 24a and the fourth reflection surface 24b of the optical path conversion unit 20 and proceeds towards the optical detector 30 after reciprocally reflecting a plurality of times.

The first, second, third, and fourth reflection surfaces 23a, 23b, 24a, and 24b as shown in FIGS. 4A and 4B may be provided to substantially extend the optical path of the second light L2 entering the optical path conversion unit 20, and thus, the second light L2 may be extend its optical path by reciprocally reflecting between the first, second, third, and fourth reflection surfaces 23a, 23b, 24a, and 24b as many times as the desire of the user. The user may optionally control the detection of the second light L2 at the optical detector 30 after the optical path of the second light L2 is extended in the optical path conversion unit 20 by reflecting a certain degree of times between the first, second, third, and fourth reflection surfaces 23a, 23b, 24a, and 24b.

When the second light L2 is emitted from the optical path conversion unit 20 after extending the optical path thereof by reflecting N times between the first, second, third, and fourth reflection surfaces 23a, 23b, 24a, and 24b, the optical path of the second light L2 may be extended as much as L according to the Equation 1.

$$L = N \times D \qquad \text{[Equation 1]}$$

where L indicates an extended optical path of the second light L2 by reflecting N times between the first, second, third, and fourth reflection surfaces 23a, 23b, 24a, and 24b of the optical path conversion unit 20, D indicates a distance between the first reflection surface 23a and the second reflection surface 23b or a distance between the third reflection surface 24a and the fourth reflection surface 24b. The distance D and the angle between the first, second, third, and fourth reflection surfaces 23a, 23b, 24a, and 24b may be controlled so that the optical path of the second light L2 is extended as much as desired.

The types of the optical path conversion unit 20 are not limited to the types depicted in FIGS. 4A and 4B, and thus, there is no specific limitation of type as long as the disposition may extend the optical path of the second light L2 is extended. That is, reflection surfaces that may be used in the optical path conversion unit 20 are not limited to two reflection surfaces as depicted in FIGS. 4A and 4B, a further number of reflection surfaces may be used.

In the apparatus 100 according to the current exemplary embodiment, the optical detector 30 may detect a third light L3 which is the second light L2 emitting from the optical path conversion unit 20 after the optical path thereof is converted and extended. The optical detector 30 may include a pixel array detector, and may include a plurality of image sensors arranged in a one-dimensional (1D) array structure or a two-dimensional (2D) array structure. The optical detector 30 may be, for example, a photodiode, a charge coupled device (CCD), a CMOS camera, or a CMOS image sensor (CIS). As another example, the optical detector 30 may be a position sensitive detector (PSD). The PSD may include at least two unit sensors spatially separated from each other.

Figure 5:
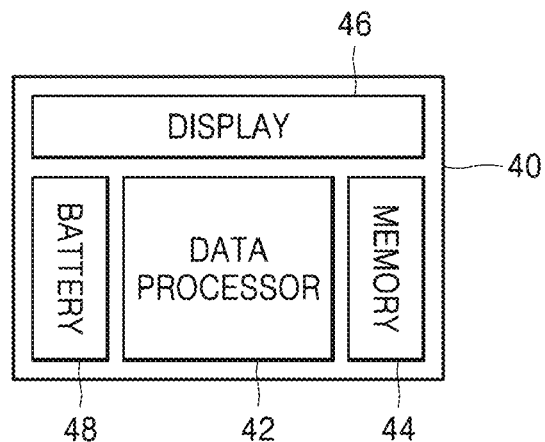
FIG. 5 is a schematic drawing of a controller of the apparatus according to an exemplary embodiment.

FIG. 5 is a schematic drawing of a controller of the apparatus according to an exemplary embodiment.

Referring to FIGS. 1 and 5, the second light L2 that has the physiological information of the object 200 and the optical path of which is converted and extended by passing through the optical path conversion unit 20 may be detected in the optical detector 30 as the third light L3. The physiological information data of the object 200 detected by the optical detector 30 may be analyzed by the controller 40. The controller 40 may obtain physiological information of the object 200 by interpreting and analyzing the physiological information data detected by the optical detector 30 in a data processor 42. The data processor 42 may obtain physiological information of the object 200 and also may perform classifying the speckles, comparison of the measured speckle pattern and a speckle pattern obtained in advance, and image processing by using the speckle pattern obtained from the second light L2 that is scattered from the object 200.

The apparatus 100 according to the current exemplary embodiment may continuously measure the physiological information of the object 200, and an algorithm that analyses the physiological information of the object 200 by using the speckle pattern obtained from the second light L2 may be stored in a memory 44 besides the measured speckle pattern and the physiological information of the object 200. The apparatus 100 according to the current exemplary embodiment may continuously perform the collection and analysis work of physiological information of the object 200 without an additional support from an external device. The controller 40 may include a display 46 to visually display the measured speckle pattern or to visually display to the user the result of comparison between physiological information obtained from the speckle pattern and physiological information obtained in advance. Also, the controller 40 may include a battery 48 to supply power to the optical irradiation unit 10, the optical detector 30, and the data processor 42, the memory, and the display of the controller 40.

The apparatus 100 according to the current exemplary embodiment includes the optical irradiation unit 10, the optical path conversion unit 20, the optical detector 30, and the controller 40 to analysis physiological information of the object 200. The apparatus 100 may be used together with other mobile devices, and also, may be independently used as a prototype. Also, the apparatus 100 may be mounted on a region of the object 200 as a band type, and also, may be continuously operated during moving of the object 200 by being mounted on a cloth. The apparatus 100 according to the current exemplary embodiment may be used in a small box state in which all constituent elements are included. For example, the apparatus 100 may have a size not greater than 35×35×15 mm.

Figure 6:
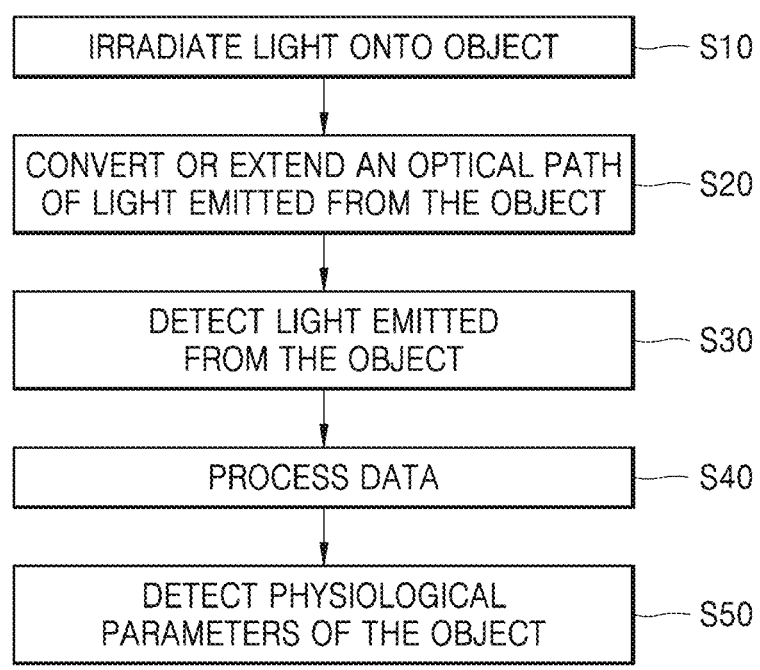
FIG. 6 is a flowchart of a method of measuring body parameters of an object by the apparatus, according to an exemplary embodiment.

FIG. 6 is a flowchart of a method of measuring physiological parameters of the object 200 by the apparatus 100 according to an exemplary embodiment.

Referring to FIGS. 1 and 6, emitting coherent light L1 onto the object 200 from the optical irradiation unit 10 of the apparatus 100 (operation S10). When light is emitted onto the object 200, a static electric field and/or a magnetic field may be applied to the object 200. At this point, the light applied to the object 200 is referred to as a first light L1. A wavelength of the first light L1 may be arbitrary selected. The apparatus 100 may be spaced apart from or in a contact state with the object 200, and there is no specific limitation in distance to the object 200.

The first light L1 applied to the object 200 is emitted as a second light L2 by scattering on a region of the object 200, for example, a skin surface of the object 200 or a blood vessel part of inner skin of the object 200. The optical path of the second light L2 may be converted by the optical path conversion unit 20 by receiving the second light L2 emitted from the object 200 (operation S20). The second light L2 may be changed to a state to obtain physiological information by converting and extending the optical path thereof by the optical path conversion unit 20.

Speckle pattern information of a region of the object 200 may be obtained by the optical detector 30 by detecting the second light L2 (operation S30). The speckle pattern information in the data processor 42 of the controller 40 may be processed by using the speckle pattern information of the object 200 obtained at the optical detector 30 (operation S40). Through the information obtained through the above processes, the physiological information, that is, physiological parameters of the object 200 may be detected (operation S50).

Figure 7:
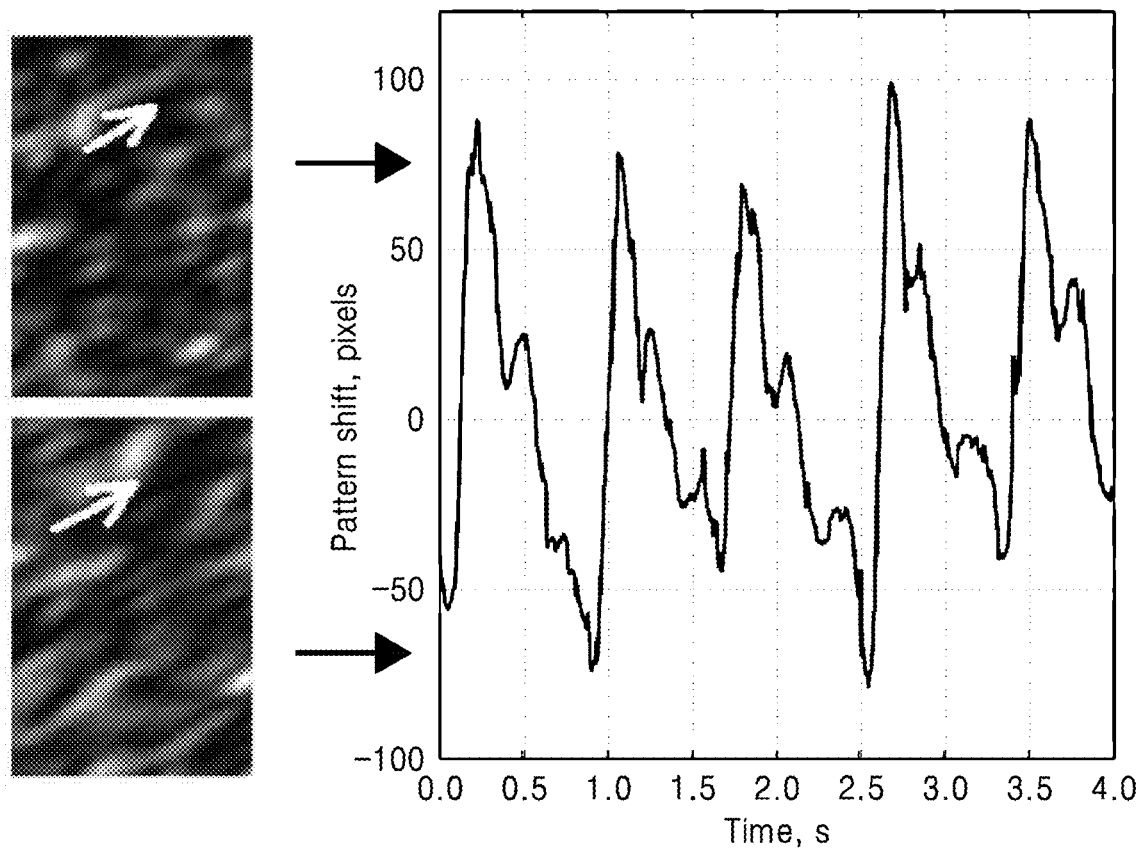
FIG. 7 shows speckle patterns measured from the object by an apparatus and a graph of transformed speckle patterns, according to an exemplary embodiment.

FIG. 7 shows speckle patterns measured from the object 200 by the apparatus 100 and a graph of transformed speckle patterns, according to an exemplary embodiment.

Referring to FIGS. 1 and 7, after emitting a coherent light, that is, the first light L1 onto a region of the object 200, for example, a skin or a blood vessel, the second light L2 scattered from the object 200 is detected by the optical path conversion unit 20, and the optical path of the second light L2 is converted and extended in the optical path conversion unit 20. In this manner, since the optical path of the second light L2 is extended or delayed, the size of the speckle pattern included in the second light L2 may become a size suitable for measuring physiological information of the object 200. For example, the second light L2 may have the optical path delayed from about 100 nm to about 300 nm by the optical path conversion unit 20, and the optical detector 30 may obtain a speckle pattern from the second light L2, the optical path of which is extended or delayed. As depicted in FIG. 7, the speckle pattern may have a predetermined distributed pattern shape on a detector plane. The extraction of a feature, classification, and analysis of the speckle pattern may be performed in the controller 40 from the obtained speckle pattern. That is, as depicted in FIG. 7, after extracting the numbers of peaks, peak shape, peak intensity, etc. from the speckle pattern information converted to a graph, the data processor 42 may compare the extracted results with information stored in the memory 44 of the controller 40. Various suitable methods of algorithms may be used to extract the specific features from the speckle pattern, for example, the Lukas-Kanade algorithm may be used.

The physiological information of the object 200, for example, systolic and diastolic blood pressures, blood flow velocity, or pulse may be analyzed through the feature extraction process as described above. When a blood pressure of the object 200 is detected after the specific features are extracted, for example, machine learning algorithms may be used. In this process, comparison may be possible between the previous user's records stored in the memory, physiological information measured by different methods, and measuring results of different users.

According to the current exemplary embodiment, an independent and miniaturized physiological information measuring apparatus configured to continuously detect physiological information of an object during normal activities of the object is provided. The physiological information measuring apparatus may be attached to a specific part of the object, and also, may be used as a wearable device by including in a cloth of the object. The wavelength of a first light may be appropriately controlled to correspond to the region of the object where the physiological information is measured. An optical path of a second light scattered from the object may be readily converted, extended, or delayed by using an optical path conversion unit.

While not restricted thereto, an exemplary embodiment can be embodied as computer-readable code on a computer-readable recording medium. The computer-readable recording medium is any data storage device that can store data that can be thereafter read by a computer system. Examples of the computer-readable recording medium include read-only memory (ROM), random-access memory (RAM), CD-ROMs, magnetic tapes, floppy disks, and optical data storage devices. The computer-readable recording medium can also be distributed over network-coupled computer systems so that the computer-readable code is stored and executed in a distributed fashion. Also, an exemplary embodiment may be written as a computer program transmitted over a computer-readable transmission medium, such as a carrier wave, and received and implemented in general-use or special-purpose digital computers that execute the programs. Moreover, it is understood that in exemplary embodiments, one or more units of the above-described apparatuses and devices can include circuitry, a processor, a microprocessor, etc., and may execute a computer program stored in a computer-readable medium.

The foregoing exemplary embodiments are merely exemplary and are not to be construed as limiting. The present teaching can be readily applied to other types of apparatuses. Also, the description of the exemplary embodiments is intended to be illustrative, and not to limit the scope of the claims, and many alternatives, modifications, and variations will be apparent to those skilled in the art.

What is claimed is:

1. A physiological parameter detecting apparatus comprising:
    a light source configured to emit a light onto a region of an object;
    an optical path converter comprising two parallel linear reflection surfaces configured to receive the light returning from the object and convert an optical path of the received light returning from the object;
    an optical detector configured to detect the light that has the converted optical path; and
    a controller configured to extract physiological information of the object from the detected light having the converted optical path,
    wherein the two parallel linear reflection surfaces comprise a first linear reflection surface and a second linear reflection surface that are spaced apart from each other in a first direction, and extend between a first end side and a second end side of the optical path converter in a second direction that is perpendicular to the first direction, and
    wherein the second linear reflection surface extends farther than the first linear reflection surface toward the first end side to receive the light from the object, and the first linear reflection surface extends farther than the second linear reflection surface toward the second end side and the optical detector to output the light having the converted optical path from the first linear reflection surface toward the optical detector, and
    wherein the optical detector is positioned farther away from the second end side of the optical path converter in the second direction, and positioned closer to the second end side than to the first end side while being apart from the second end side of the optical path converter.

2. The physiological parameter detecting apparatus of claim 1, wherein the light source is further configured to emit a coherent wave to the object.

3. The physiological parameter detecting apparatus of claim 1, wherein the light emitted from the light source has a wavelength in a range from 400 nm to 700 nm.

4. The physiological parameter detecting apparatus of claim 1, wherein the light emitted from the light source has a wavelength in a range from 700 nm to 1500 nm.

5. The physiological parameter detecting apparatus of claim 1, wherein the optical path converter is further configured to extend or delay the optical path of the received light.

6. The physiological parameter detecting apparatus of claim 1, wherein the two parallel linear reflection surfaces are arranged to face each other.

7. The physiological parameter detecting apparatus of claim 1, wherein the optical detector comprises a pixel array detector and a plurality of image sensors arranged in a one-dimensional (1D) structure or a two-dimensional (2D) structure.

8. The physiological parameter detecting apparatus of claim 1, wherein the optical detector comprises a position sensitive detector (PSD) comprising at least two sensors spatially separated from each other.

9. The physiological parameter detecting apparatus of claim 1, wherein the controller comprises a data processor, a memory, a display, and a battery.

* * * * *